United States Patent
Peters et al.

(10) Patent No.: US 7,977,514 B2
(45) Date of Patent: Jul. 12, 2011

(54) PROCESS FOR ISOLATION OF AN ORGANIC AMINE

(75) Inventors: Alexander V. Peters, Aachen (DE); Gerardus J. P. Krooshof, Sittard (NL); Nicolaas M. H. Beckers, Cadier en Keer (NL); John Krijgsman, Maastricht (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 12/160,349

(22) PCT Filed: Dec. 20, 2006

(86) PCT No.: PCT/EP2006/012307
§ 371 (c)(1), (2), (4) Date: Jul. 27, 2009

(87) PCT Pub. No.: WO2007/079944
PCT Pub. Date: Jul. 19, 2007

(65) Prior Publication Data
US 2010/0274057 A1    Oct. 28, 2010

(51) Int. Cl.
*C07C 209/82* (2006.01)
*C07C 209/84* (2006.01)
*C07C 209/86* (2006.01)

(52) U.S. Cl. .................................. 564/497; 564/498

(58) Field of Classification Search .................. 564/497, 564/498
See application file for complete search history.

(56) References Cited

U.S. PATENT DOCUMENTS

| | | | | |
|---|---|---|---|---|
| 3,151,163 A | * | 9/1964 | Nussbaum | 564/481 |
| 3,492,354 A | | 1/1970 | Cywinski | |
| 3,849,496 A | * | 11/1974 | Forster | 564/497 |

FOREIGN PATENT DOCUMENTS

JP    2004-000114    1/2004

OTHER PUBLICATIONS

International Search Report for PCT/EP2006/012307, mailed Mar. 15, 2007.
Written Opinion for PCT/EP2006/012307, mailed Mar. 15, 2007.
Database WPI Week, Derwent Publications, JP 2004-000114, Jan. 2004, XP002423726.

* cited by examiner

Primary Examiner — Brian J Davis
(74) Attorney, Agent, or Firm — Nixon & Vanderhye P.C.

(57) ABSTRACT

The invention relates to a process for the isolation of an organic amine from a composition comprising the organic amine and an acid, or a salt of the organic amine and the acid, wherein the process comprises steps wherein ammonia or hydrazine is added to the composition thereby forming a multi-phase system comprising an organic amine-rich phase and an acid-rich phase, the organic amine-rich phase and the acid-rich phase obtained in step (i) are separated, and the organic amine is isolated from the organic amine-rich phase.

23 Claims, 3 Drawing Sheets

PROCESS FOR ISOLATION OF AN ORGANIC AMINE

This application is the U.S. national phase of International Application No. PCT/EP2006/012307, filed 20 Dec. 2006, which designated the U.S. and claims priority to European Patent Application No. 06075067.6, filed 11 Jan. 2006, the entire contents of each of which are hereby incorporated by reference.

FIELD

The invention relates to a process for the isolation of an organic amine from a composition comprising the organic amine and an acid, or a salt of the organic amine and the acid.

BACKGROUND AND SUMMARY

Such a process is known from the Japanese patent applications JP-2004222569-A and JP-2004000114-A. In the known process of JP-2004000114-A the organic amine is 1,5-pentanediamine, an organic amine also known as cadaverine, produced by a fermentative route wherein L-lysine decarboxylase is allowed to act on an L-lysine salt water solution and the L-lysine salt is for example a hydroclorite, sulfate, acetate, nitrate or carbonate. The system comprising the cadaverine is an aqueous solution and the acid in the salt is hydrochloric acid, sulfuric acid, acetic acid, nitric acid or carbonic acid. The cadaverine is said to be isolated from the reaction solution by adding alkali to the solution, wherein the alkali is any one of sodium hydroxide, potassium hydroxide and calcium hydroxide, thereby raising the pH to 12-14, and subsequently the cadaverine is extracted with a polar solvent, such as aniline, cyclohexanone, 1-octanol, isobutyl alcohol, cyclohexanol, and chloroform. A similar process is also described in JP-2004222569-A. JP-2004222569-A further describes an alternative process for isolation of the cadaverine from the solution. In the alternative process an organic solvent is added without the use of an alkali. The organic solvent is chosen from alcohol, ketones and nitriles. The acid is hydrochloric acid or a dicarboxylic acid, for example, adipic acid, sebacic acid, succinic acid or terephthalic acid. In the alternative process, the cadaverine is isolated in the form of its salt with hydrochloric acid or the dicarboxylic acid. The cadaverine as well as the salt of cadaverine with the dicarboxylic acid are said to be useful as raw material for producing polyamide.

A disadvantage of the first known process is that it produces by-products in the form of an aqueous solution comprising dissolved alkali acid salts next to a surplus of either alkali or acid, which solution results in a significant loss of material in the process, or alternatively would require complicated additional processing steps for isolating the salt, the acid and/or the alkali from the aqueous solution. Moreover, when the process of JP-2004000114-A was reworked by the inventors with for example chloroform, it showed not work to in a significant extent, if it worked at all. The alternative known process has the disadvantage that amine impurities, which are also formed in fermentative processes, easily incorporate into the cadaverine acid salt. When such non-purified cadaverine dicarboxylic acid salt is used for making a polyamide, polymerization will result in polyamides with less good properties or polymerization is even not feasible at all. On the other hand, it is very difficult if not possible at all to remove the impurities from the cadaverine dicarboxylic acid salt with simple industrial processes.

The aim of the invention is to provide a process for the isolation of an organic from a composition comprising the organic amine and an acid, or a salt of the organic amine and the acid, which process does not show the disadvantages of the first known process and the alternative known process or in a lesser extent.

This aim has been achieved with the process according to the invention, which process comprises steps wherein:
(i) ammonia or hydrazine is added to the composition thereby forming a multi-phase system comprising an organic amine-rich phase and an acid-rich phase,
(ii) the organic amine-rich phase and the acid-rich phase obtained in step (i) are separated, and
(iii) the organic amine is isolated from the organic amine-rich phase.

It has surprisingly been found that the addition of ammonia or hydrazine in a sufficient amount to a composition comprising the organic amine and the acid, or a salt of the organic amine and the acid, results in formation of a multi-phase system comprising an organic amine-rich phase and an acid-rich phase. Consequently, the organic amine-rich phase is lean in acid content, if any acid is present at all, whereas the acid-rich phase is reduced in amine content, if any amine is still present at all. It has also surprisingly been found that the organic amine has a preferred solubility in, or miscibility with an ammonia- and/or hydrazine-rich phase, whereas the salts of acids with ammonia or hydrazine have a very low solubility in, or miscibility with such a phase, explaining for the formation of a separate phase when ammonia and/or hydrazine is added in a sufficient amount. The advantage of the process according to the invention is that separation of the organic amine and the acid is accomplished in one single step, i.e. by adding the ammonia and/or the hydrazine, instead of two steps in the first known process cited above. Furthermore, the organic amine can be isolated from the ammonia and/or the hydrazine containing phase, and any amine impurities therein, by simple measures. Further advantages are that the ammonium and hydrazonium acid salts formed as a by-product can more easily be separated from the surplus ammonia or hydrazine, and that the surplus of ammonia or hydrazine can be more easily recovered free of the by-product salts and reused in the isolation process.

An organic amine is herein understood to be a compound comprising at least one amine functional group covalently bonded to at least one carbon atom.

The organic amine that can be used in the process according to the invention can be any amine that is soluble in water, either as such or as a salt with an acid and which amine is soluble in ammonia- or hydrazine-rich phase.

Suitably, the organic amine is a primary amine, a secondary amine or a tertiary amine, i.e. an organic amine comprising respectively a primary amine functional group, a secondary amine functional group, or a tertiary amine functional group. A primary amine functional group is herein understood to be a mono-substituted amine functional group covalently bonded to one carbon atom, a secondary amine functional group is herein understood to be a di-substituted amine functional group covalently bonded to two carbon atoms, and a tertiary amine functional group is herein understood to be a tri-substituted amine functional group covalently bonded to three carbon atoms. The substituents covalently bonded to the amine functional group may be linear, branched, saturated or unsaturated, and/or comprise a ring structure. The substituents covalently bonded to the amine functional group may suitably comprise one or more hetero-atoms. A hetero-atom is herein understood to be an atom not being carbon or hydrogen Suitable organic amines that can be used in the process according to the invention include, for example, aliphatic amines and aromatic amines, combinations thereof and hetero-atom substituted derivatives thereof. Suitable organic amines also include hetero-atom substituted amines and cyclic amines, or a combination thereof.

Aliphatic amines are herein understood to be amines comprising one or more aliphatic groups covalently bonded to the amine functional group. Suitable aliphatic amines are alkyl amines, cycloalkyl amines and cycloalkylalkyl amines. Examples of suitable alkylamines are butylamine and hexylamine; a suitable cycloalkyl amine is cyclohexylamine; a suitable cycloalkylalkyl amine is di(aminomethyl)cyclohexane. Examples of suitable primary amines are methylamine, ethylamine, propylamine, hydroxypropylamine and cyclonexylamine; examples of suitable secondary amines are dimethylamine, diethylamine and diethanolamine, and examples of suitable tertiary amines include triethylamine and triethanolamine.

Aromatic amines are herein understood to be amines comprising one or more aromatic groups covalently bonded to the amine functional group. The aromatic amines can be aromatic substituted amines and aralkyl amines. Suitable aralkyl amines are benzyl amine, and xylylenediamine, suitable aromatic substituted amines include aniline and amphetamine. Suitable hetero-atom substituted derivatives are the hydroxyethylamines mentioned above and heterocyclic substituted amines, for example melamine, 6-phenyl-2,4,7-pteridinetriamine, and 2-amino-5-phenyl-4(5H)-oxazoline. An example of a suitable hetero-atom substituted amine is 2-(2-6-dichlorophenoxy)ethylaminoguanadine. Suitable cyclic amines include pyrolidine, pyridine, indole, and combinations thereof.

The organic amine that is used in the process according to the invention suitably comprises monoamines, diamines, triamines and polyamines, as well as mixtures thereof. The diamines suitably are primary amines, secondary amine or tertiary amines, or a combination thereof. The triamines and polyamines suitably comprise secondary amine functional groups, or a combination of secondary amine functional groups with one or more primary amine functional groups and or tertiary amine functional groups.

Examples of suitable diamines are butanediamine, pentanediamine and hexanediamine. A suitable polyamine is for example polyethyleneamine.

Preferably, the organic amine comprises a diamine, more preferably, a diamine chosen form the group consisting of 1,4-butanediamine, 1,5-pentanediamine, 1,6-hexanediamine, and mixtures thereof. The advantage thereof is that these diamines are very well suited for making polyamides.

Also preferably, the organic amine comprises a compound having an equivalent weight per amine functional group of at most 100, preferably in the range of 35-80, more preferably 40-60. The advantage of an organic amine having a lower equivalent weight per amine functional group is that the organic amine has a better solubility in the ammonia or hydrazine-rich liquid phase.

Also preferably, the organic amine has a molecular weight below 200. The advantage is that the organic amine is more easily isolated from the liquid phase by distillation.

The acid that may be present in the composition comprising the organic amine may be any acid that can be transferred into an ammonium or hydrazonium salt that is insoluble or immiscible, or nearly so, in an ammonia- and/or hydrazine-rich phase. Whether an acid is suitable for that purpose can simply be tested by making a concentrated aqueous solution of an ammonium or hydrazonium salt of the acid in water, and adding ammonia. If a precipitate is formed upon addition of ammonia the acid is suitable. The lower the concentration of the salt in the concentrated aqueous solution can remain for forming the precipitate and/or the lower the amount of ammonia that is needed for forming the precipitate, the more suited the acid is.

Suitably, the acid comprises an inorganic acid, an organic acid or a combination thereof. Suitable inorganic acids include compounds chosen form the group consisting of hydrochloric acid, sulfuric acid, sulfonic acid, nitric acid, phosphoric acid, phosphonic acid, and mixtures thereof. Examples of suitable organic acids are carboxylic acids, including dicarboxylic acids, and short chain and long chain monocarboxylic acids. Particularly suitable are low molecular weight or short chain carboxylic acids (C1-C4), which short chain carboxylic acids include the preferred compounds chosen form the group consisting of carbonic acid (C1), acetic acid (C2) and propionic acid (C3), and mixtures thereof.

Preferably, the acid comprises an inorganic acid, more preferably the inorganic acid comprises sulfuric acid or phosphoric acid, or a mixture thereof. The advantage of sulfuric acid or phosphoric acid comprised in the acid is that the ammonium or hydrazonium salt formed therewith can be re-used as a nitrogen feed stock in a fermentation process for preparing the organic amine, Still more preferably, the acid consists of sulfuric acid or phosphoric acid. Most preferably, the acid consists of sulfuric acid. The advantage of the acid consisting of sulfuric acid is that the ammonium or hydrazonium salt thereof, which will be formed sulfuric acid during the process according to the invention can be reused as a nitrogen feedstock in a fermentative process for preparing the organic amine.

The composition comprising the organic amine and an acid, or a salt of the organic amine and the acid, suitably is a solid or a liquid. When the composition is a solid, the organic amine and the acid are conveniently present in the composition in the form of the salt of the organic amine and the acid. The solid composition may comprise further components next to the organic amine acid salt. The organic amine, or the salt thereof, may be present in the solid composition in a concentration varying over a large range. This range depends on the type of organic amine as well as on the type of acid that is used in combination with the organic amine. Suitably, the organic amine and the acid are present in the solid composition in a total amount in the range of 50-100 wt. %, preferably 70-100 wt. %, more preferably 90-100 wt. %, and most preferably 99-100 wt. %, relative to the total weight of the solid composition.

When the composition comprising the organic amine and the acid, or salt thereof, is a solid, the ammonia or hydrazine that is added and brought into contact with the solid suitably is a gas or a liquid. When the ammonia or hydrazine is a gas, the organic amine can be stripped from the solid, thereby forming a gaseous or liquid ammonia- or hydrazine-rich phase containing the organic amine. When the ammonia or hydrazine is a liquid, the organic amine can be extracted from the solid, thereby forming a liquid ammonia- or hydrazine-rich phase containing the organic amine. The solid phase will gradually become reduced in organic amine content. To intensify the contact between the solid and the ammonia or hydrazine, the solid can be stirred.

Preferably, when the composition comprising the organic amine and the acid is a solid, the ammonia or hydrazine is a liquid. This has the advantage that less ammonia or hydrazine is needed for isolating the organic amine from the composition.

When the composition is a liquid, the composition suitably is an aqueous solution. The organic amine, or the salt thereof, may be present in the aqueous solution in a concentration varying over a large range. This range depends on the type of organic amine as well as on the type of acid that is used in combination with the organic amine. Suitably, the organic amine is present in a concentration of at least 1 wt. %, relative to the total weight of the aqueous solution, preferably at least 2 wt. %, or even at least 5 wt. %, 10 wt. %, 20 wt. %, and most preferably at least 30 wt. % relative to the total weight of the aqueous solution. The advantage of a higher concentration is that the effect of the invention is further enhanced and that significant less ammonia or hydrazine needs to be added to form the two-phase system with the precipitate of the ammonium or hydrazonium salt of the acid.

Advantageously, the aqueous solution is concentrated prior to step (i) of the process according to the invention, thereby increasing the organic amine and acid or salt thereof. The aqueous solution may be concentrated by any method that is suitable for that purpose, for example by water evaporation or by reverse osmosis. Evaporation can be accomplished for example by distillation. Preferably, reverse osmosis is applied as the method for concentration of the aqueous solution. The advantage of reverse osmosis that this process can be performed under more moderate temperatures. Reverse osmosis is therefore advantageously applied for products, which are sensitive for forming side products under the conditions of distillation, thereby reducing the formation of side products.

The ammonia or hydrazine that is added to the aqueous solution must be added in an amount that is sufficient to form a multi-phase system. The amount that is needed depends on the concentration of the organic amine and the acid in the aqueous solution, the choice of ammonia or hydrazine, as well as factors like temperature. Likewise the ammonia or hydrazine is added in a slight or larger excess to assure that the ammonium or hydrazonium acid salt is precipitated as quantitative as possible. The amounts needed for forming the multi-phase system and for quantitative precipitation of the salt can be determined by the person skilled in the art by routine measurements.

In a preferred embodiment of the process according to the invention, in step (i) ammonia is added to the aqueous solution. The advantage of ammonia is that it is cheap, widely available, and, most importantly, a valuable nitrogen feedstock in fermentative processes. Ammonia can be used either as a gas or a liquid whilst the applied pressure can remain very moderate.

The aqueous solution in the process according to the invention suitably is obtained from a process stream resulting from a process for preparing the organic amine. The process for preparing the organic amine may be any process, and suitably is a conventional chemical process. Preferably the process for preparing the organic amine is a fermentative process.

In a preferred embodiment of the invention, the aqueous solution is obtained from a process stream resulting from a fermentative process, the aqueous solution comprises sulfuric acid and/or phosphoric acid as the acid, and ammonia is added in step (i) to form the two-phase system. The advantage of this embodiment is that precipitate that is formed comprises ammonium sulfate and/or ammonium phosphate, which can be easily isolated with the process according to the invention and reused as nitrogen feedstock in the fermentative process.

In another preferred embodiment of the invention, the aqueous solution is obtained from a process stream resulting from a fermentative process for the preparation of a diamine, preferably butane diamine, pentane diamine, and/or hexane diamine.

In several embodiments of the invention, the organic amine-rich phase is a liquid phase and the acid-rich phase is a solid phase.

For the separation of the solid phase and the liquid phase in step (ii) of the process according to the invention any method that is suitable for separating solid and liquid phases may be applied. Suitable methods are, for example, filtration methods, sedimentation methods, and spraying methods. Suitable methods for separating solid and liquid phases are described, for example, in Kirk Orthmer Encyclopaedia of chemical technology.

A suitable sedimentation method is, for example, a method wherein centrifugation is applied. In this method a sediment with a supernatant liquid is formed, which supernatant liquid can, for example, be decanted. Suitably, the sedimentation is carried out in a hydrocyclone. Suitably, the hydrocyclone is connected to an evaporator for separating high volatile and low volatile components, which are further separated in respectively a high pressure distillation column and a low pressure distillation column.

Preferably, the liquid phase and solid phase are separated in a hydrocyclone. Such a process has the advantage that it process can be carried out more easily as a continuous process.

For the isolation of the organic amine from the liquid phase in step (iii) of the process according to the invention any method that is suitable for isolating compounds from liquid phases may be applied. Suitable methods are, for example, distillation methods, sedimentation methods and extraction methods, and combinations thereof.

A suitable distillation method is, for example, a method wherein the ammonia or hydrazine is distilled off. This method is suitably applied for organic diamines, which are liquids at room temperature and/or at the temperature range at which the ammonia or hydrazine is distilled off.

A suitable sedimentation method is, for example, a method wherein a solvent is added which is miscible with ammonia or hydrazine, but which is a non-solvent for the organic amine. This method is suitably applied where the organic amine is a solid material at room temperature. The advantage of the sedimentation method where the organic amine is a solid material at room temperature is that upon addition of the solvent the organic amine will precipitate from the liquid phase, and than can be isolated by the usual methods for isolating a solid from a liquid phase.

A suitable extraction method is, for example, a method wherein a solvent is added which is not miscible with ammonia or hydrazine and which is a good solvent for the organic amine.

Preferably, the organic amine is isolated from the liquid phase by distillation, wherein the ammonia and/or hydrazine is distilled off. The advantage of this isolation method is that there is no need for addition of another solvent or non-solvent. A further advantage of this method is that it can more easily be applied for a process wherein the organic amine consists of a mixture of amines including liquid amines, which amines need to be separated and isolated further.

Therefore, the distillation is preferably performed as a fractionated distillation. The fractioned distillation may suitably be performed in one or more steps. With the fractioned distillation performed in more steps, suitably in the first step low boiling fractions and high boiling fractions are separated and then in a second, and optionally further steps, the low boiling fractions and/or high boiling fractions are further separated, thereby obtaining the components in the liquid phase with higher purity.

The isolation by distillation is suitable performed under reduced pressure, and/or at elevated temperature.

A further advantage of the isolation by distillation is that the ammonia or hydrazine that is obtained from the distillation does not comprise organic solvents and can be reused in step (i) of the inventive process.

The process according to the invention comprising isolation of the organic amine by distillation, is suitably performed in an installation as depicted in FIG. 1, FIG. 2 or FIG. 3.

For those embodiments of the invention, where the organic amine-rich phase is a gas phase, the organic amine may be isolated from that phase by any method that is suitable for isolating volatile components from gaseous phases. Suitably, the organic amine is isolated by selectively, condensing, distilling and condensing operations.

DETAILED DESCRIPTION

Figure 1:
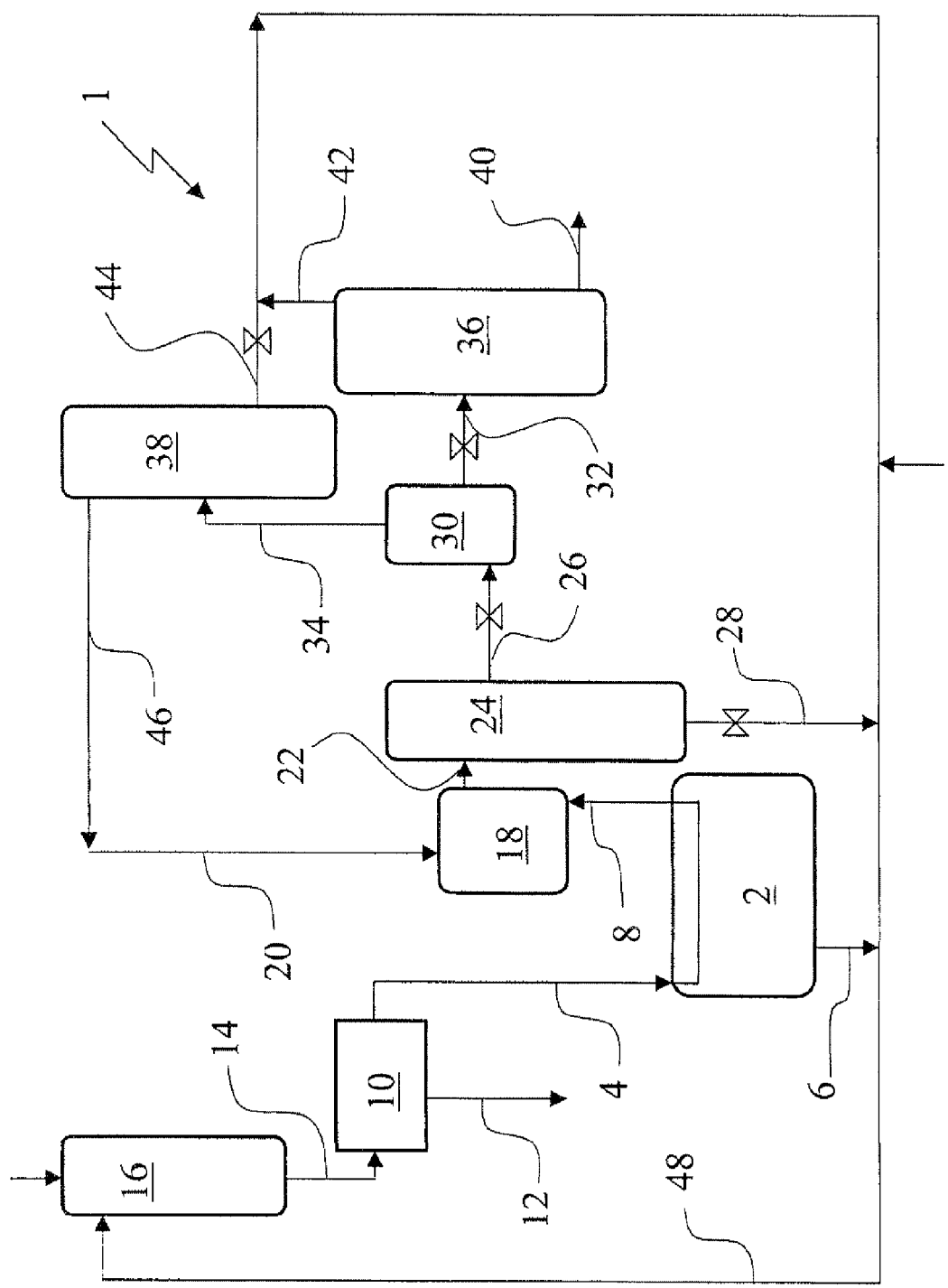
FIG. 1, FIG. 2 and FIG. 3 show each a schematic lay-out of an installation suitable for carrying out the isolation process according to the invention integrated in a production process for the preparation of organic amine.

FIG. 1 shows a schematic lay-out of an installation suitable for 1 carrying out the isolation process according to the invention. The installation (1) of FIG. 1 comprises membrane unit (2) provided with an inlet tube (4) and outlet tubes (6) and (8). The inlet tube (4) is connected to a separator unit (10), which separator unit (10) is provided with an outlet tube (11) and connected via a connection tube (12) to a reactor (14). Outlet tube (8) is connected to a mixer (16). The mixer is further provided with an inlet tube (18) and an outlet tube (20). Outlet tube (20) is connected to a hydrocyclone (21a), equipped with outlets (21b) and (21c). Outlet (21a) is connected to an evaporator unit (22). Evaporator unit (22) is provided with 2 outlet tubes (22) and (24), which are connected respectively to a low-pressure distillation column (26) and a high-pressure distillation column (28). The low-pressure distillation column (26) is provided with two outlets, a lower outlet tube (30), and an upper outlet tube (32). The high-pressure distillation column (28) is also provided with two outlets, a lower outlet (34), and an upper outlet (36). The upper outlet (36) can be connected to the inlet tube (18). One or more of the lower outlet (34), the upper outlet tube (32), the outlet (21b) and the outlet (6) may be connected to an inlet tube (38) connected to the reactor (16)

In the installation of FIG. 1, a process stream comprising the organic amine, and corning from the reactor (14) via the connecting tube (12), the separator (10) and the inlet tube (4) can be fed to the membrane unit (2). By applying a reverse osmosis process in the membrane unit water may be separated form the process stream whereby the process stream is concentrated. The water may be released form the outlet (6) and the concentrated process stream can be fed via outlet (8) to the mixer (16). Via inlet tube (18) ammonia and/or hydrazine can be fed to the mixer (16) and mixed with the concentrated process stream, thereby forming a multiphase system comprising a liquid and a solid phase. The mixture can be fed via the outlet tube (20) to the hydrocyclone (21a), wherein the liquid and the solid phase can be separated. The liquid phase can be via outlet tube (21b) to the evaporator unit (22). In the evaporator unit (22), the liquid phase can be separated into a low-pressure boiling fraction and a high-pressure boiling fraction. The low-pressure boiling fraction can be fed via outlet tube (22) to the low-pressure distillation column (26) and the high-pressure boiling fraction can be fed via outlet tube (24) to the high-pressure distillation column (28). In the low-pressure distillation column (26) the ammonia or hydrazine can be separated from other components in the low-pressure boiling fraction and optionally be fed back to the mixer (16) via outlet tube (32). In the high-pressure distillation column (28) the organic amine can be separated from other components in high-pressure boiling fraction and released via outlet tube (38).

Optionally, waste streams or secondary streams coming from the membrane unit (2), the hydrocyclone (21a), the low-pressure distillation column (26) and/or the high low-pressure distillation column (26) may optionally be fed back to the reactor (16) via inlet tube (48).

Figure 2:
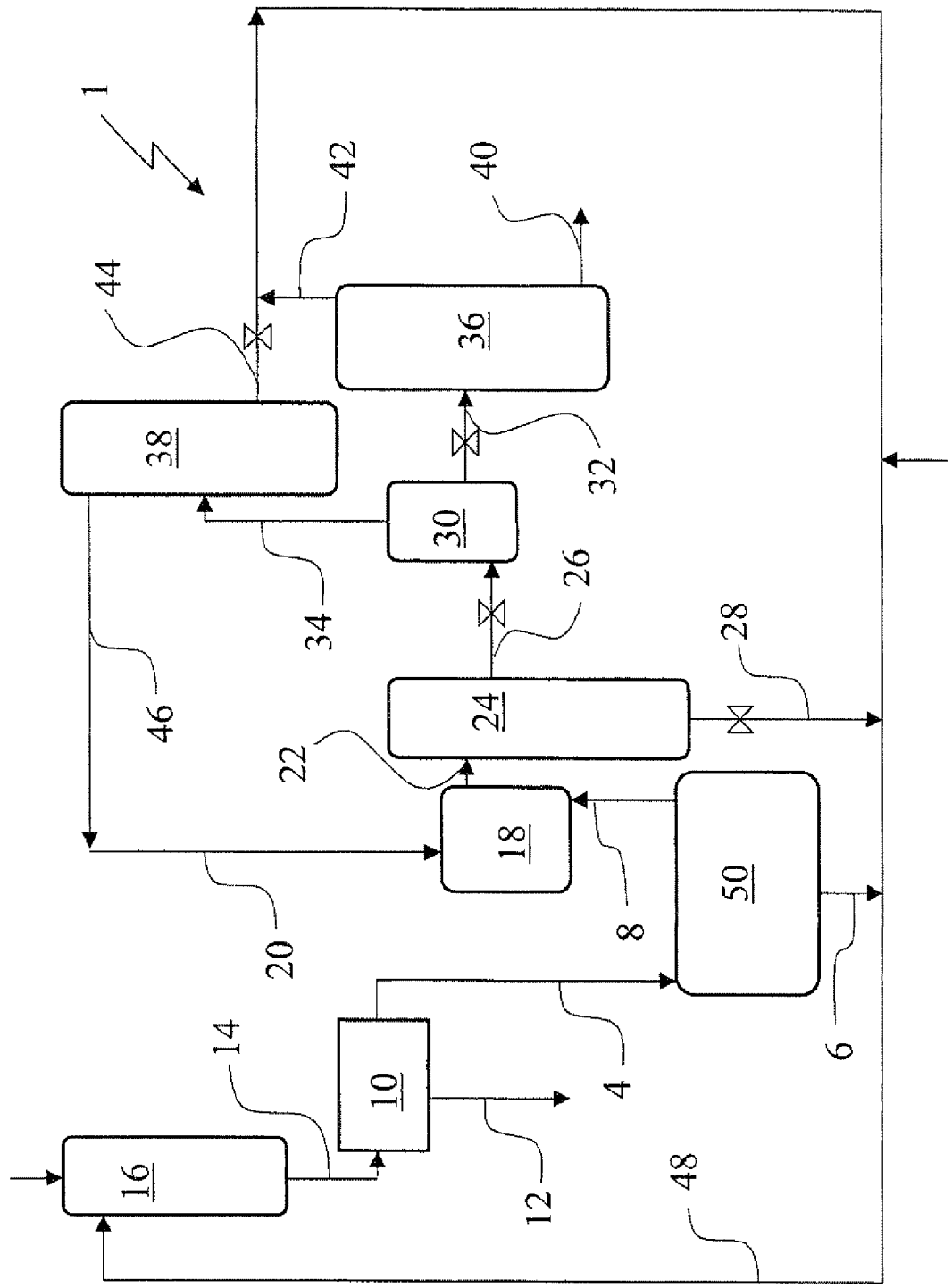

FIG. 2 shows a schematic lay-out of an installation suitable for carrying out the isolation process according to the invention, analogous to that of FIG. 1, except that the membrane unit (2) has been replaced with an evaporator (40). In the evaporator the process stream can be concentrated by distillation.

Figure 3:
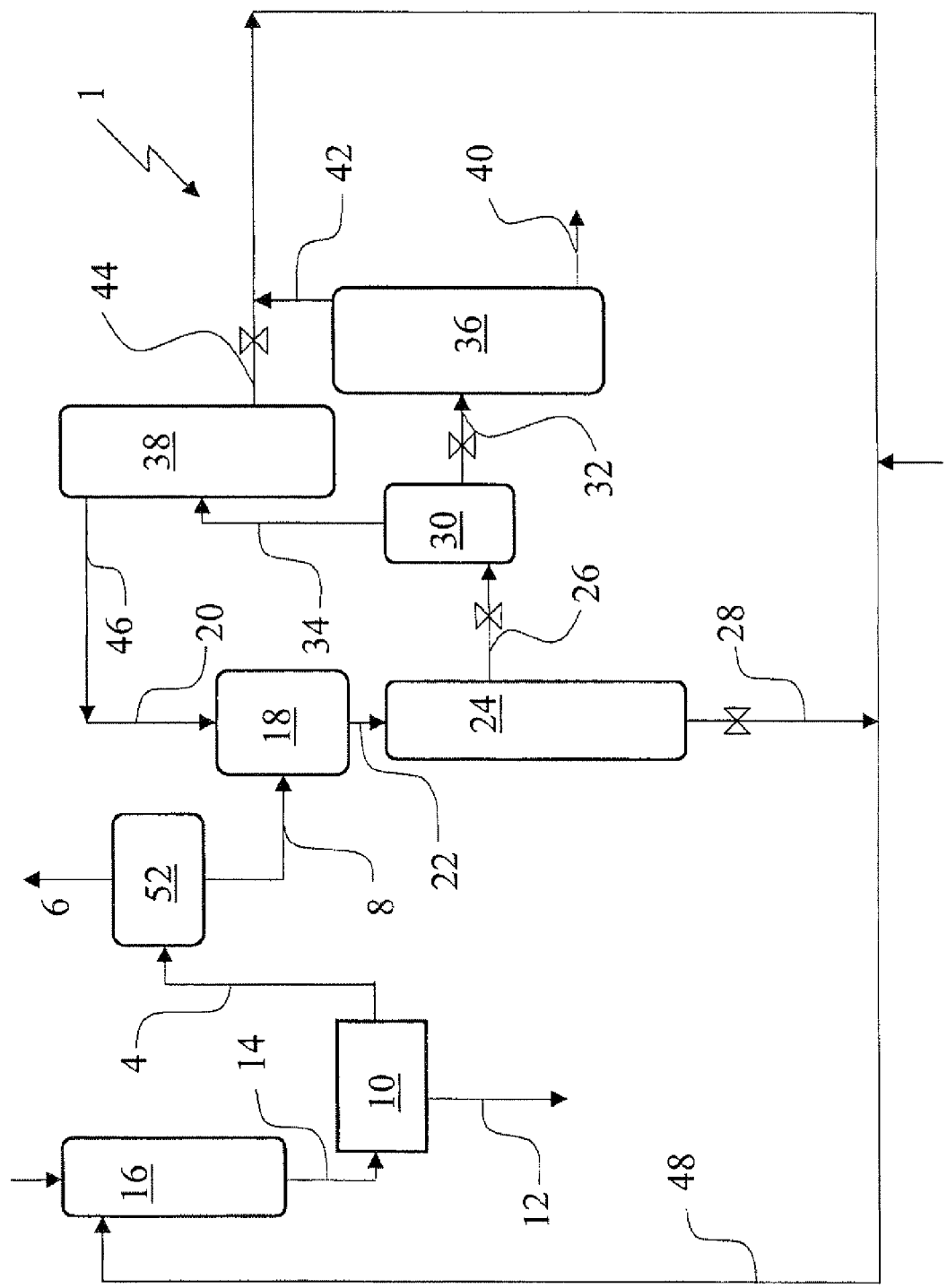

FIG. 3 shows a schematic lay-out of an installation suitable for carrying out the isolation process according to the invention, analogous to that of FIG. 1, except that the membrane unit (2) has been replaced with a crystallizer (42). In the crystallizer, the organic amine can be isolated from the process stream in the form of its salt with the acid. In this case it is the salt that is fed to the mixer (16).

The invention is further illustrated with the following Examples and Comparative Experiments.

Analytical Methods

Sulfate ion ($SO_4^{2-}$) content was determined with ion chromatography on a low capacity anion exchange column.

Ammonium ion ($NH4^-$) content was determined with ion chromatography on a low capacity cation exchange column.

Amine content was determined with HPLC. Prior to the determination, the amines were derivatised by treating the amine containing samples with NBD-chloride, than the sample was injected into the HPLC apparatus, upon which the derivatives separated by chromatography and detected with fluorescence.

Chloroform content was determined with GC-FID using a non-polar column. Quantification was done by internal standard method.

Materials

The following amines were used: 1,2-diaminoethane, 1,4-diaminobutane, 1,5-diaminopentane, 1,6-diaminohexane, and 1-aminobutane.

EXAMPLE I

In a 1.5 autoclave 353 g aqueous 1,4-diaminobutane (67 wt. % in water) and subsequently 712 g aqueous sulfuric acid (37 wt. % in water) were added and mixed to make a solution of 500 g 1,4-diammonium butane sulfate in 565 g water. The solution was heated to 80° C. at normal pressure, than vacuum was applied to distill off the water. A solid dry salt was obtained. Analysis showed that the molar ratio of 1,4-diaminobutane and $SO_4^{2-}$ to be close to 1. This salt was used for next step. 550 g Liquid pure ammonia was added to 495 g of the 1,4-diammonium butane sulfate salt under continuous stirring. The slurry was stirred for 1 hour. After the stirring was stopped, solid particles settled down and a supernatant liquid was formed. The composition of the supernatant liquid was analyzed as follows. 9.1 g of the liquid was sampled into 881 g of water. The aqueous solution was analyzed from which followed that the liquid sample contained 11.2 wt. % 1,4-diaminobutane, 88.4 wt. % ammonia and less than 0.5 wt. % $SO_4^{2-}$. The molar ratio 1,4-diaminobutane: $SO_4^{2-}$ was calculated to be $\geq 24.4$.

EXAMPLE II

In a 1.5 autoclave 160 g aqueous 1,4-diaminobutane (67 wt. % in water), 322 g aqueous sulfuric acid (37 wt. % in water) and 84 g water were added to make a solution of 226 g 1,4-diammonium butane sulfate and 340 g water. A sample of 45 g was taken. Analysis showed that the concentration of 1,4-diaminobutane, $SO_4^{2-}$, and water in the sample was 20, 21 and 59 wt. % respectively. Hence the starting solution contained 41 wt. % of 1,4-diammonium butane sulfate. Liquid pure ammonia was added slowly to the remaining aqueous solution (521 g). Solids were formed directly in the liquid pool, but dissolved by stirring. When 200 ml ammonia (corresponding with about 120 g), was fed the solids formed did not dissolve again. When a total amount of 380 ml ammonia (corresponding with about 230 g) was added the agitator was stopped and after solid particles had settled down a sample of the liquid was taken. Analysis showed that the concentration of 1,4-diaminobutane, $SO_4^{2-}$, ammonia and water in the sample was 17.6, 3.5, 40 and 38.9 wt. % respectively. The molar ratio 1,4-diaminobutane:$SO_4^{2-}$ was calculated to be 5.5.

COMPARATIVE EXPERIMENT A

In a 1.5 autoclave 85 g aqueous 1,4-diaminobutane (67 wt. % in water), 171 g aqueous sulfuric acid (37 wt. % in water) and 344 g water were added to make a solution of 120 g 1,4-diammonium butane sulfate and 480 g water. A sample of 33 g was taken. Liquid pure ammonia was added slowly to the remaining aqueous solution (567 g). Solids were formed directly in the liquid pool, but dissolved by stirring. When a total amount of 350 ml ammonia (corresponding with about 210 g) was added the agitator was stopped. A clear solution without solids is obtained.

Examples 1 to 2 and Comparative Experiment a show that the lower the amount of water the better the 1,4-diaminobutane can be separated from the sulfate.

EXAMPLE III

In a 1.5 autoclave 66 g 1,6-diaminohexane, 149 g aqueous sulfuric acid (37 wt. % in water) and 87 g water were added to make a solution of 121 g of 1,6-diammonium hexane sulfate and 181 g of water. A sample of 31 g was taken. Liquid pure ammonia was added slowly to the remaining aqueous solution (271 g). Solids were formed directly in the liquid pool, but dissolved by stirring. When 190 ml (about 114 g) ammonia was added the formed solids did not dissolve again. When 260 ml (about 156 g) ammonia was added, stirring was stopped, solids were settled down a sample of the resulting liquid phase was taken. The liquid phase was analyzed and showed that the concentration of 1,6-diaminohexane, $SO_4^{2-}$, ammonia and water in the sample was 11.8, 4.4, 35.0 and 48.8 wt. % respectively. The molar ratio of 1,6-diaminohexane:$SO_4^{2-}$ was calculated to be 2.2,

EXAMPLE IV

In a 1.5 autoclave 60 g 1,2-diaminoethane, 265 g aqueous sulfuric acid (37 wt. % in water) and 70 g water were added to make a solution of 158 g of 1,2-diammonium ethane sulfate and 237 g of water, Liquid pure ammonia was added slowly. Solids were formed directly in the liquid pool, but dissolved by stirring. When 190 ml (about 114 g) ammonia was added, the formed solids did not dissolve anymore. When 260 ml (about 156 g) ammonia was added, the stirring was stopped, solids were settled down and a sample of the resulting liquid phase was taken. The liquid phase was analyzed and showed that the concentration of 1,2-diaminoethane, $SO_4^{2-}$, ammonia and water in the sample was 10.5, 3.0, 39.0 and 47.5 wt. % respectively. The molar ratio of 1,2-diaminoethane:$SO_4^{2-}$ was calculated to be 5.6.

EXAMPLE V

In a 1.5 autoclave 146 g 1-aminobutane, 265 g aqueous sulfuric acid (37 wt. % in water) and 199 g of water were added to make a solution of 244 g of di(n-butylammonium) sulfate and 366 g of water. A sample of 15 g was taken. Liquid pure ammonia was added slowly. Solids were formed directly in the liquid pool, but dissolved by stirring. When 180 ml (about 108 g) ammonia was added the formed solids did not dissolve anymore. When 404 ml (about 242 g) ammonia was added, stirring was stopped, the solids were settled down a sample of the resulting liquid phase was taken, The liquid phase was analyzed and shows that the concentration of 1-aminobutane, $SO_4^{2-}$, ammonia and water in the sample was 17.4, 2.6, 33.3 and 46.7 wt. % respectively. The molar ratio 1-aminobutane:$SO_4^{2-}$ was calculated to be 17.3, which is 8.65 times better than the molar ratio in the salt di-(1-ammonium butane) sulfate.

EXAMPLE VI

In a 1.5 autoclave 68 g 1,5-diaminopentane (cadaverine), 175 g aqueous sulfuric acid (37 wt. % in water) and 136 g of water were added to make a solution of 133 g of 1,5-diammonium pentane sulfate and 246 g of water. Liquid pure ammonia was added slowly. Solids were formed directly in the liquid pool, but dissolved by stirring. When 195 ml (about 117 g) ammonia was added, the formed solids did not dissolve anymore. When 480 ml (about 288 g) ammonia is added, the stirring was stopped, solids are settled down a sample of the resulting liquid phase was taken. The liquid phase is analyzed and shows that the concentration of 1,5-diaminopentane, $SO_4^{2-}$, ammonia and water in the sample was 8.7, 0.8, 50.4 and 40.1 wt. % respectively. The molar ratio 1,2-diaminopentane:$SO_4^{2-}$ was calculated to be 10.2.

COMPARATIVE EXAMPLE B

In a 1.5 liter autoclave 91 g 1,5-diaminopentane (cadaverine), 175 g aqueous hydrogenchloride (37 wt. %) and 350 g of water were added to make a solution of 156 g of 1,5-diammonium pentane chloride and 460 g of water. The acidity was measured: pH=8. To the solution 10 g KOH tablets were added. The acidity of the solution was measured again showed to have become pH>11. To the solution 666 g of Chloroform (450 ml) were added. The resulting total volume was 995 ml. After stirring for one hour two liquids were present, a upper liquid phase of 575 ml, and a lower liquid phase of 420 ml. Both liquid phases were sampled and analyzed. The upper liquid phase showed to be an aqueous phase and contained 14.3 wt. % cadaverine, 0.4 wt % Chloroform and 10.1 wt. % Cl⁻ ions; the rest was primarily water. The lower liquid phase showed to be an organic phase and contained <0.1 wt. % cadaverine, 94.0 wt. % chloroform and 11 ppm Cl⁻; the rest was primarily water.

The latter result show that the cadaverine is still almost completely present in the aqueous solution comprising the chloride ions, and that pH correction with potassium hydroxide and extraction with chloroform gives a poor yield of cadaverine.

The invention claimed is:

1. A process for the isolation of an organic amine from a composition comprising the organic amine and an acid, or a salt of the organic amine and the acid, wherein the process comprises the steps of:
   (i) adding ammonia or hydrazine to the composition in an amount sufficiently large to form a precipitate of an ammonium or hydrazonium salt of the acid and to thereby form a multi-phase system comprising an organic amine-rich phase and an acid-rich phase comprised of the ammonium or hydrazonium salt of the acid,
   (ii) separating the organic amine-rich phase and the acid-rich phase obtained in step (i), and
   (iii) isolating the organic amine from the organic amine-rich phase.

2. The process according to claim 1, wherein the organic amine is a diamine, pentane diamine or hexane diamine, or a mixture thereof.

3. The process according to claim 1, wherein the acid comprises an inorganic acid or a short chain carboxylic acid.

4. The process according to claim 1, wherein the acid comprises sulfuric acid or phosphoric acid, or a mixture thereof.

5. The process according to claim 1, wherein the composition is a solid and the ammonia or hydrazine is a liquid.

6. The process according to claim 1, wherein the composition is an aqueous solution.

7. The process according to claim 6, wherein the organic amine is present in the aqueous solution in a concentration of at least 1 wt. %, relative to the total weight of the aqueous solution.

8. The process according to claim 6, wherein the aqueous solution is concentrated prior to step (i).

9. The process according to claim 6, wherein in step (i) ammonia is added to the aqueous solution.

10. The process according to claim 6, wherein the aqueous solution is obtained from a process stream resulting from a process for preparing the organic amine.

11. Process according to claim 1, wherein the organic amine-rich phase is a liquid phase and the acid-rich phase is a solid phase, and the liquid phase and solid phase are separated by spraying.

12. Process according to claim 1, wherein the organic amine-rich phase is a liquid phase, and wherein step (iii) comprises isolating the organic amine from the liquid phase by distillation, and optionally reusing the ammonia or hydrazine that is obtained from the distillation in step (i).

13. The process according to claim 1, wherein the organic amine comprises butane diamine.

14. The process according to claim 10, wherein the process stream results from a fermentative process.

15. A process for the isolation of an organic amine from a composition comprising the organic amine and an acid, or a salt of the organic amine and the acid, wherein the process comprises:
   (i) adding ammonia or hydrazine to the composition to thereby form a multi-phase system comprising an organic amine-rich phase and an acid-rich phase,
   (ii) separating the organic amine-rich phase and the acid-rich phase obtained in step (i), and
   (iii) isolating the organic amine from the organic amine-rich phase, wherein
   the acid comprises sulfuric acid or phosphoric acid, or a mixture thereof.

16. A process for the isolation of an organic amine from a composition comprising the organic amine and an acid, or a salt of the organic amine and the acid, wherein the process comprises:
   (i) adding ammonia or hydrazine to the composition to thereby form a multi-phase system comprising an organic amine-rich phase and an acid-rich phase,
   (ii) separating the organic amine-rich phase and the acid-rich phase obtained in step (i), and
   (iii) isolating the organic amine from the organic amine-rich phase, wherein
   the composition is a solid and the ammonia or hydrazine is a liquid.

17. A process for the isolation of an organic amine from an aqueous solution comprising the organic amine and an acid, or a salt of the organic amine and the acid, wherein the process comprises:
   (i) adding ammonia or hydrazine to the aqueous solution to thereby form a multi-phase system comprising an organic amine-rich phase and an acid-rich phase,
   (ii) separating the organic amine-rich phase and the acid-rich phase obtained in step (i), and
   (iii) isolating the organic amine from the organic amine-rich phase.

18. The process according to claim 17, wherein the organic amine is present in the aqueous solution in a concentration of at least 1 wt. %, relative to the total weight of the aqueous solution.

19. The process according to claim 17, wherein the aqueous solution is concentrated prior to step (i).

20. The process according to claim 17, wherein in step (i) ammonia is added to the aqueous solution.

21. The process according to claim 17, wherein the aqueous solution is obtained from a process stream resulting from a process for preparing the organic amine.

22. The process according to claim 21, wherein the process stream results from a fermentative process.

23. A process for the isolation of an organic amine from a composition comprising the organic amine and an acid, or a salt of the organic amine and the acid, wherein the process comprises:
   (i) adding ammonia or hydrazine to the composition to thereby form a multi-phase system comprising an organic amine-rich phase and an acid-rich phase,
   (ii) separating the organic amine-rich phase and the acid-rich phase obtained in step (i), and
   (iii) isolating the organic amine from the organic amine-rich phase, wherein
   the organic amine-rich phase is a liquid phase and the acid-rich phase is a solid phase, and the liquid phase and solid phase are separated by spraying.

* * * * *